(12) United States Patent
Fubara et al.

(10) Patent No.: US 9,005,652 B2
(45) Date of Patent: Apr. 14, 2015

(54) CHEWABLE TABLET CONTAINING PHENYLEPHRINE

(75) Inventors: Josephine Fubara, Richmond, VA (US); Mark Mabry, Chesterfield, VA (US); Aaron Lewis Durr, Glen Allen, VA (US); Angela Taylor, Chester, VA (US); Amanda Alley, Midlothian, VA (US); David H. Giamalva, Glen Allen, VA (US); Manish Agrawal, Gaithersburg, MD (US)

(73) Assignee: Wyeth, Madison, NJ (US)

( * ) Notice: Subject to any disclaimer, the term of this patent is extended or adjusted under 35 U.S.C. 154(b) by 2149 days.

(21) Appl. No.: 11/492,656

(22) Filed: Jul. 25, 2006

(65) Prior Publication Data

US 2008/0026055 A1    Jan. 31, 2008

(51) Int. Cl.
*A61K 9/20*      (2006.01)
*A61K 31/137*    (2006.01)
*A61K 9/00*      (2006.01)

(52) U.S. Cl.
CPC ............. *A61K 31/137* (2013.01); *A61K 9/0056* (2013.01)

(58) Field of Classification Search
None
See application file for complete search history.

(56) References Cited

U.S. PATENT DOCUMENTS

| | | | |
|---|---|---|---|
| 928,264 A | 7/1909 | Lourie et al. | |
| 3,039,922 A | 6/1962 | Berger et al. | |
| 3,400,197 A | 9/1968 | Lippmann et al. | |
| 3,629,394 A | 12/1971 | Gaunt et al. | |
| 4,632,821 A | 12/1986 | Peters et al. | |
| 4,753,800 A | 6/1988 | Mozda | |
| 4,942,236 A | 7/1990 | Musser et al. | |
| 4,946,684 A | 8/1990 | Blank et al. | |
| 5,013,716 A * | 5/1991 | Cherukuri et al. | 514/23 |
| 5,348,747 A | 9/1994 | Bianco | |
| 5,681,577 A * | 10/1997 | Lech et al. | 424/439 |
| 6,187,340 B1 | 2/2001 | Fukuta et al. | |
| 6,509,492 B1 | 1/2003 | Venkataraman | |
| 2001/0009678 A1 | 7/2001 | Toshihiro et al. | |
| 2003/0060422 A1 | 3/2003 | Venkataraman | |
| 2003/0083354 A1 * | 5/2003 | Kiel et al. | 514/352 |
| 2005/0020509 A1 * | 1/2005 | Kiel et al. | 514/23 |
| 2007/0249566 A1 * | 10/2007 | Martin et al. | 514/165 |

FOREIGN PATENT DOCUMENTS

| | | |
|---|---|---|
| EP | 0 559 463 A1 | 4/1993 |
| EP | 0 404 490 B1 | 7/1993 |
| EP | 0 996 424 B1 | 5/1998 |
| EP | 0 785 770 B1 | 10/2000 |
| JP | 2004 269517 A | 6/2006 |
| WO | WO 02/41920 A | 5/2002 |
| WO | WO 03/009834 A | 2/2003 |
| WO | WO 03/011306 A | 2/2003 |
| WO | WO 2006/064327 | 6/2006 |
| WO | WO 2007/143155 A2 | 12/2007 |
| WO | WO 2007/143156 A1 | 12/2007 |

\* cited by examiner

*Primary Examiner* — Nissa Westerberg
(74) *Attorney, Agent, or Firm* — Jeffrey Gold; Joseph F. Reidy

(57) ABSTRACT

A chewable pharmaceutical composition comprising phenylephrine, artificial sweetener, and a substantially aldehyde-free matrix is provided. The composition has phenylephrine stability suitable for a typical commercial product with a two year shelf life. A method of manufacture of the composition and a method of use are also provided.

13 Claims, No Drawings

CHEWABLE TABLET CONTAINING PHENYLEPHRINE

FIELD OF THE INVENTION

A chewable pharmaceutical composition comprising phenylephrine is provided. The composition is particularly well suited for the relief of cold, cough, flu, fever, headache, pain, body ache, migraine, and allergy symptoms.

BACKGROUND OF THE INVENTION

Many commercially available over-the-counter oral cold, cough, flu, fever, and/or allergy preparations contain pseudoephedrine as an active agent. Although such preparations have been useful, misuse of such products as a starting material for synthesis of illicit substances has lead to the desire to find alternatives that are not suitable for such illicit synthesis. Phenylephrine is a potential alternative active. However, phenylephrine is susceptible to degradation. The degradation is typically facilitated in excipient compositions of the type typically used with pseudoephedrine.

Orally administered pharmaceutical compositions are provided to patients in many dosage forms, including solid forms such as capsules, caplets or tablets and liquid forms such as solutions, suspensions and liquid fill for capsules. For many patients including young children, older persons and incapacitated persons, a chewable dosage form is preferable because of the ease with which it may be ingested.

Accordingly, it would be desirable to have a palatable, chewable dosage form comprising phenylephrine with reduced propensity for degradation of phenylephrine.

SUMMARY OF THE INVENTION

The pharmaceutical composition described herein is a chewable oral pharmaceutical composition comprising phenylephrine, an artificial sweetener, and a substantially aldehyde free matrix. The composition has less than 2.5 wt/wt % total isoquinolines and maintains said level of isoquinolines for at least 24 months.

The composition may further comprise one or more second active agents selected from analgesics, decongestants, expectorants, anti-tussives, antipyretics, anti-inflammatory agents, cough suppressants and antihistamines.

In one embodiment mannitol may be used as a diluent.

The composition may be formed in the absence of liquid water at ambient temperatures.

DETAILED DESCRIPTION OF THE INVENTION

The invention provides an oral chewable pharmaceutical composition comprising the pharmaceutical active phenylephrine. The composition is palatable and has improved phenylephrine stability. The inventors believe with out wishing to be bound to the theory that the selection of substantially aldehyde-free excipients and avoidance of liquid water and/or heat in the manufacturing process enhance phenylephrine stability. The composition comprises phenylephrine, an artificial sweetener, and a substantially aldehyde free matrix. Roller compaction is exemplary of a suitable method of tableting the composition that avoids use of liquid water with the composition in the manufacturing process and may be accomplished without adding heat (e.g. at ambient temperature).

Prior to the invention, solid compositions comprising phenylephrine HCl were found to be susceptible to the formation of significant levels of isoquinoline degradants (often observed in amounts >4%). Phenylephrine containing solid compositions are typically more susceptible to the formation of isoquinoline degradants than phenylephrine HCl containing liquid oral dosage forms. The solid phenylephrine comprising composition described herein comprises less than 2.5% wt/wt total isoquinolines and maintains said isoquinolines level for at least 24 months. More preferably the composition comprises less than 1.5% wt/wt total isoquinolines and maintains said isoquinoline level for at least 24 months.

Phenylephrine HCl has several degradation pathways that form isoquinolines. The inventors believe without wishing to be bound to the theory that a primary pathway for the formation of isoquinloline degradants in prior phenylephrine HCl compositions is the interaction of Phenylephrine HCl with aldehydes present from flavors and other excitipients used in the prior compositions. The aldehydes may be an added component as in the case of some flavors, for example, or may be the result of impurities in or degradation products of one or more excipients. Moisture, and in some cases the presence of a reducing sugar, also appear to facilitate the formation of isoquinolines Additionally, heat may facilitate degradation by oxidative pathways.

Accordingly, the inventors have discovered that degradation of phenylephrine including degradation to isoquinoline in solid phenylephrine composition may be reduced by use of substantially aldehyde-free excipients including substantially aldehyde-free flavors and minimizing the degradation of excipients. The avoidance of liquid water and heat in the manufacturing process facilitates minimizing degradation products. The use of roller compaction as the granulation process is exemplary of a suitable manufacturing process.

Roller compaction is a dry granulation process involving the compression of a blended powder between rollers to produce a solid mass of material. After granulation, this material is milled to a uniform particle distribution with an even distribution of active ingredients. The lack of introduction of water and excess heat to the blend during granulation minimizes any degradation from moisture and heat while providing a consistent granulation mixture.

In an exemplary embodiment, the oral chewable composition of the invention comprises phenylephrine HCl as the active ingredient, microcrystalline cellulose, a non-sugar based sweetening system and substantially aldehyde-free diluent. The tablet granulation is manufactured using a roller compaction process to minimize any process related degradation.

The composition may contain one or more additional pharmaceutical actives (also referred to as "active(s)", "active agent(s)", "therapeutic agent(s)", "drug(s)"). Herein reference to "first pharmaceutical active" means phenylephrine and reference to "second pharmaceutical active" means any active other than phenylephrine. Further, the term second pharmaceutical active may refer to a single species of active or a plurality of species of actives other than phenylephrine (e.g., the total number of actives in the compositions may be greater than 2.)

"Substantially aldehyde-free" means no components with known aldehyde functionality or components which have aldehyde impurity levels greater than 1% or components which are know to readily degrade to aldehydes in the presence of the tablet matrix disclosed herein are included in the composition. The impurity level may be achieved by section of highly pure ingredients and/or removal of aldehydes.

"Matrix" means all components of the composition other than the active agent(s) and the artificial sweetener including, but not limited to, flavorants, colorants, fillers, binders, disintegrants, preservatives, buffers, natural sweeteners, lubricants, milling agents, glidants, anti-adherents, dispersants, thickeners, solubilizing agents and diluents.

A "chewable tablet" means a tablet that is formulated to be masticable by a mammal. Such tablets typically have a hardness of about 3-20 KPa, but hardness may vary depending on size and shape of the tablet and the propensity of the components to solubilize in saliva. Such dosage forms may be administered without water and are particularly useful for administration to pediatric patients.

Unless specified otherwise amounts are provided in milligrams per dosage unit which is abbreviated as mg/du. Percentages unless otherwise indicated are in weight percent.

Preferably the phenylephrine is in a salt form. Suitable salt forms include, but are not limited to, phenylephrine hydrochloride (HCl), hydrobromide (HBr), bitartarate and tannate salts. Phenylephrine may be used in an amount of about 0.5 to about 30.0 mg/dosage unit. Preferably, phenylephrine is used in an amount of about 2.5 to about 5.0 mg/dosage unit.

An artificial sweetener is provided to improve palatability. An artificial sweetener is preferred for use as a sweetener to the use of conventional sugar sweeteners as the inventors believe, without wishing to be held to the theory, that conventional reducing sugars may contribute to the degradation of phenylephrine. Suitable artificial sweeteners, include but are not limited to sucralose, saccharine salts, cyclamates, acesulfame K, dipeptide based sweeteners, aspartame and mixtures thereof. Sucralose, which is a high intensity sweetener, is particularly well suited for use in the composition. Sucralose may be used in an amount of about 1% wt/wt to about 10% wt/wt, for example. The appropriate amount of artificial sweetener depends on properties and sweetness intensity of the artificial sweetener and target organoleptic properties of the composition. One skilled in the art is familiar with the characteristics of sweeteners and methods for determining amount of sweetener to be used.

Suitable additional or second active agents include analgesics, decongestants, expectorants, anti-tussives, antipyretics, anti-inflammatory agents, cough suppressants and antihistamines.

Antihistamines useful in the practice of the present invention (along with their preferred salt form) include, but are not limited to, chlorpheniramine (maleate), brompheniramine (maleate); dexchlorpheniramine (maleate), dexbrompheniramine (maleate), triprolidine (HCl), diphenhydramine (HCl, citrate), doxylamine (succinate), tripelenamine (HCl), cyproheptatine (HCl), chlorcyclizine (HCl), bromodiphenhydramine (HCl), phenindamine (tartrate), pyrilamine (maleate, tannate), azatadine (maleate); acrivastine, astemizole, azelastine, cetirizine, ebastine, fexofenadine, ketotifen, carbinoxamine (maleate), desloratadine, loratadine, pheniramine maleate, thonzylamine (HCl), mizolastine and terfenadine.

Antitussives useful in the practice of the present invention (along with their preferred salt form) include, but are not limited to, chlophendianol, caramiphen (ediylate), dextromethorphan (HBr), diphenhydramine (citrate, HCl), codeine (phosphate, sulfate) and hydrocodone.

Decongestants useful in the practice of the invention (along with their preferred salt form) include, but are not limited to, pseudoephedrine (HCl, sulfate), Ephedrine (HCl, Sulfate), phenylephrine (bitartarate, tannate, HBr, HCl), and phenylpropenolamine (HCl).

Expectorants which may be used in the practice of the invention (along with their preferred salt form) include but are not limited to terpin hydrate, guaifenesin (glycerol, guaiacolate), potassium (iodide, citrate) and potassium guaicolsulfonate.

Non-steroidal anti-inflammatory drugs (NSAIDS) which may be used in the practice of the invention include, but are not limited to, propionic acid derivatives such as ibuprofen, naproxen, ketoprofen, flurbiprofen, fenoprofen, suprofen, fluprofen and fenbufen; acetic acid derivatives such as tolmetin sodium, zomepirac, sulindac, and indomethacin; fenamic acid derivatives such as mefenamic acid and meclofenamate sodium; biphenyl carboxylic acid derivatives such as diflunisal and flufenisal and oxicams such as piroxicam, sudoxicam and isoxicam.

Cox 2 inhibitors which may be used in the practice of the invention include, but are not limited to, Celecoxib, Rofecoxib and Valdecoxib.

Analgesics which may be used in the practice of the invention include but are not limited to aspirin, acetominophen, phenacetin and salicylate salts.

Amounts of pharmaceutically active compounds incorporated are conventional dosages known to those skilled in the art. Further, for pharmaceutical compositions intended for use in the United States, amounts of pharmaceutical actives are preferably in compliance with applicable FDA regulations regarding dosage of such compounds.

Of the pharmaceutically active compounds described above which may be included in addition to phenylephrine in the composition, those which are particularly preferred are set forth below along with preferred ranges for their inclusion into the claimed pharmaceutical composition.

Chlorpheniramine may be used in the pharmaceutical composition in amounts between about 1 mg/du and about 8 mg/du. Preferably chlorpheniramine, when used in the pharmaceutical composition, is present in the amount of about 1 mg/du to about 4 mg/du.

Brompheniramine maleate may be used in the pharmaceutical composition, preferably in the amount of about 1 mg/du to about 4 mg/du.

Dextromethorphan HBr may be used in the pharmaceutical composition, in the amount of about 15 mg/du to about 30 mg/du.

Guaifenesin may be used in the composition in amounts of about 25 mg/du to about 200 mg/du and preferably in amounts of about 25 mg/du to about 100 mg/du.

Acetaminophen may be used in the composition in amounts of about 60 mg/du to about 1000 mg/du and preferably in amounts of about 60 mg/du about 325 mg/du.

Chlophedianol may be used in the composition in amounts of about 10 mg/du to about 25 mg/du.

Diphenhydramine may be used in the composition in amounts of about 5 mg/du to about 50 mg/du and preferably in amounts of about 5 mg/du to about 25 mg/du.

Loratadine may be used in the composition in amounts of about 2.5 mg/du to about 10 mg/du and preferably in amounts of about 2.5 mg/du to about 5.0 mg/du.

Aspirin may be used in the composition in amounts of about 160 mg/du to about 650 mg/du and preferably in amounts of about 160 mg/du to about 320 mg/du.

Doxylamine may be used in the composition in amounts of about 3.7 mg/du to about 25 mg/du and preferably in amounts about 3.75 mg/du to about 12.5 mg/du.

The pharmaceutically active compounds are preferably of a compendial grade such as, for example, of N.F. (National Formulary) or U.S.P. (United States Pharmacopeia) grade.

Excipients known by those skilled in the art may be useful in the practice of the present invention. Such excipients may include, but are not limited to, flavorants, colorants, fillers, binders, disintegrants, preservatives, pH adjustment agents, natural sweeteners, lubricants, milling agents, glidants, antiadherents, dispersants, thickeners, solubilizing agents, diluents, preservatives, antioxidants, and taste masking agents.

Diluents useful in the practice include polyols such as mannitol. Diluents with aldehyde functionality, aldehyde impurities, or a propensity to form aldehyde degradants are preferably avoided. For the materials tested, the inventors found tablets made with mannitol, to be less susceptible to degradation than tablets made with sorbitol or xylitol. It is not known if this is due to inherently superior properties of mannitol or whether this is due to specific features of the lots of material tested.

Anti-oxidants may be included in the composition. Propyl gallate is exemplary of an antioxidant that is suitable for use in the composition.

Dicarboxylic and tricarboxylic organic acids may be used as pH adjustment agents Fumaric acid and citric acid are exemplary of suitable pH adjustment agents. It is preferable to adjust the composition to maintain the pH less than about 6 when placed in water.

Coloring agents may also be incorporated in the pharmaceutical composition to provide an appealing color to the composition. The coloring agents should be selected to avoid chemical incompatibilities with other ingredients in the composition. Suitable coloring agents are well known to those skilled in the art.

A binder may be included in the composition. Exemplary binders include, but are not limited to, polyethylene oxide, hydroxypropylmethyl cellulose (i.e., HPMC or hypromellose), and povidone.

Lubricants suitable for use in the composition include, but are not limited to stearic acid, magnesium stearate, and glyceryl behenate.

Microcrystalline cellulose is exemplary of a filler suitable for use in the practice of the invention. Microcrystalline cellulose is commercially available from suppliers such as FMC (1735 Market Street, Philadelphia, Pa. 19103) under the trade name Avicell™

Typically, addition of a flavorant is desirable in a chewable tablet to enhance palatability. The flavorant should be substantially free of aldehyde functionality. Accordingly, it is desirable that to both avoid flavors with aldehyde functionality and flavors provided in a medium that contains aldehydes. Addition of a flavorant is desirable in a chewable tablet. Examples of suitable flavorants include, but are not limited to, natural and artificial flavors such as mints (i.e., peppermint, etc.), menthol, chocolate, artificial chocolate, bubblegum, both artificial and natural fruit flavors (i.e., cherry, grape, orange, strawberry, etc.), debittering flavors and combinations of two or more thereof. Flavoring agents are generally provided in the composition in amounts effective to provide palatable flavor to the compositions. Typically, flavoring agents are present in amounts in the range of about 0 grams to about 5 grams per 100 grams of the composition.

Agents which adjust "mouth feel" (e.g. organoleptic properties) may be included in the composition. Glycine and kappa caragenen are exemplary of agents which adjust "mouth feel". Glycine may be used in amounts of about 2 to about 20 mg/du, for example Glidants may be included in the composition. Silicon dioxide is exemplary of a suitable glidant.

Optionally, preservatives may be included in the composition. Preservatives useful in the present invention include but are not limited to sodium benzoate, sorbates, such as potassium sorbate, salts of edetate (also known as salts of ethylenediaminetetraacetic acid or EDTA, such as disodium edetate), benzaldionium chloride and parabens (such as methyl, ethyl, propyl, and butyl p-hydroxybenzoic acid esters). Preservatives listed above are exemplary, but each preservative must be evaluated on an experimental basis, in each formulation to assure compatibility and efficacy of the preservative. Methods for evaluating the efficacy of preservatives in pharmaceutical formulations are known to those skilled in the art. Sodium benzoate and disodium edetate are the presently preferred preservative ingredients.

Excipients should be selected and amounts adjusted such that the composition exhibits good flow properties under gravity flow conditions, have cohesive properties and be compressible. For example, addition of a binder and/or adjustment of the amount of binder may be used to facilitate compressibility.

In an exemplary embodiment, the active agent(s) is pre-blended with a diluent, binder and other excipients in a mixing vessel such as, for example, a V-Blender. Upon mixing, the resulting blend, may be fed, typically by gravity, to the hopper of a roller compactor.

In a typical roller compaction process, a vertical feed screw (i.e., a "VFS") facilitates feeding the blend into the compactor by deareating the blend and forcing it between the rolls. A horizontal feed screw (i.e., a "HVS") within the hopper feeds the material to VFS. The feed screw speeds (rpm) of the VFS and HFS may be adjusted to optimize the amount of blend going into the roll nip region of the roller compactor. In one exemplary embodiment the ratio of VFS:HFS speed is about 3:1.

The blend is densified and granulated, as it passes between two high-pressure rolls that compress the blend. Controlling and monitoring roll speed (which impacts dwell time for the material to be compacted by the rolls), roll pressure (which is the pressure applied to the rolls) and/or roll gap (which is a function of the pressure applied to the rolls and the material passing between them) facilitates maintaining uniformity and batch-to-batch reproducibility.

The compacted material is collected and passed thru a mill for particle sizing. Once sized the compacted material may be tableted directly or blended with additional ingredients and tableted.

Roller compaction is exemplary of one method for preparing the composition of the invention. Other dry granulation methods such as slugging, for example, may be likewise suitable.

Typically, the composition is provided to a patient in need of treatment in a dosage unit of 1-2 tablets per dosage units although other dosage units may be likewise suitable. The dosage unit may be provided as a single dosage unit or multiples thereof, based on age, weight and other health parameters determined by a physician to be relevant.

EXAMPLE 1

An exemplary composition comprising the single first pharmaceutical active phenylephrine is provided in Table 1. This composition is representative and one of many composition that are within the scope of the invention. The exemplary embodiment is provided for illustrative purposes.

TABLE 1

| Ingredient | Amount (mg/du) |
| --- | --- |
| Phenylephrine HCl | 2.50 |
| Mannitol | 175 |

TABLE 1-continued

| Ingredient | Amount (mg/du) |
|---|---|
| Microcrystalline Cellulose (MCC) | 75 |
| Fumaric acid | 21 |
| Glycine | 15 |
| Color | 1 |
| Artificial Sweetener | 5 |
| Flavorant | 10 |
| Magnesium stearate | 2.5 |
| Polyethylene oxide | 17 |

The composition of Table 1 may be prepared by roller compaction as described herein.

EXAMPLE 2

An exemplary composition comprising phenylephrine and a second active Brompheniramine maleate is provided in Table 2. This composition is representative and one of the many compositions that are within the scope of the invention. The exemplary embodiment is provided for illustrative purposes.

TABLE 2

| Ingredient | Amount (mg/du) |
|---|---|
| Phenylephrine HCl | 2.5 |
| Brompheniramine Maleate | 1 |
| Mannitol | 175 |
| Microcrystalline Cellulose | 75 |
| Fumaric acid | 21 |
| Glycine | 15 |
| Colorant | 1 |
| Artificial flavor | 10 |
| Magnesium stearate | 2.5 |
| Polyethylene oxide | 17 |

The composition of Table 2 may be prepared by roller compaction as described herein.

EXAMPLE 3

Table 3 provides degradation data for an exemplary embodiment of the composition of the invention comprising substantially aldehyde-free excipients and a similar composition comprising an aldehyde containing flavorant.

TABLE 3

| Sample | Condition (Temperature °C./% relative humidity) | Time point (week) | % Degradants |
|---|---|---|---|
| Substantially Aldehyde Free composition | Ambient | Initial | 0.071 |
| | 40/75 | 2 | .089 |
| | 40/75 | 4 | .070 |
| | 40/75 | 8 | .100 |
| | 40/75 | 12 | 0.339 |
| | 40/75 | 16 | 0.284 |
| Composition with Aldehyde containing flavorant (vanilla) | Ambient | Initial | 0.524 |
| | 40/75 | 2 | 1.705 |
| | 40/75 | 4 | 2.392 |
| | 40/75 | 8 | 3.253 |

TABLE 3-continued

| Sample | Condition (Temperature °C./% relative humidity) | Time point (week) | % Degradants |
|---|---|---|---|
| | 40/75 | 12 | 4.831 |
| | 40/75 | 16 | 4.159 |

EXAMPLE 4

Table 4 provides degradation data for an exemplary embodiment of the composition of the invention comprising substantially aldehyde-free excipients prepared by roller compaction and a similar composition prepared by wt granulation methods.

TABLE 4

| Sample | Condition (Temperature °C./% relative humidity) | Time point (week) | % Degradants |
|---|---|---|---|
| Composition prepared by Roller Compaction | Ambient | Initial | 0.071 |
| | 40/75 | 2 | .089 |
| | 40/75 | 4 | .070 |
| | 40/75 | 8 | .100 |
| | 40/75 | 12 | 0.339 |
| | 40/75 | 16 | 0.284 |
| Composition prepared by Wet Granulation | 40/75 | 16 | 1.039 |

Although the foregoing invention has been described in some detail by way of illustrations and examples for purposes of clarity of understanding, it will be obvious that certain changes and modifications may be practiced within the scope of the appended claims. Modifications of the above-described modes of practicing the invention that are obvious to persons of skill in the art are intended to be included within the scope of the following claims.

What is claimed is:

1. A chewable composition comprising:
   a). about 2.5 mg/dosing unit phenylephrine;
   b). sucralose;
   c.) brompheniramine maleate;
   c). a matrix comprising substantially aldehyde-free excipients and an substantially aldehyde-free flavorant; and
   d.) wherein the composition is free of sodium benzoate, sorbates, salts of edetate (EDTA), benzaldionium chloride and parabens and further comprises less than 2.5% wt/wt total isoquinolines and maintains said level of isoquinolines for at least 24 months.

2. The composition of claim 1, wherein the composition further comprises less than 1.5% wt/wt total isoquinolines and maintains said level of isoquinolines for at least 24 months.

3. The composition of claim 1, wherein the substantially aldehyde-free flavorant is selected from the group consisting of mints, menthol, chocolate, artificial chocolate, bubblegum, artificial fruit flavors, natural fruit flavors, debittering flavors and combinations thereof.

4. The composition of claim 1, wherein the matrix comprises an antioxidant.

5. The composition of claim 4, wherein the antioxidant is propyl gallate.

6. The composition of claim 1, wherein the matrix comprises mannitol.

7. A chewable tablet comprising:
a). phenylephrine;
b). sucralose;
c.) brompheniramine maleate;
c). a matrix comprising substantially aldehyde-free excipients and an aldehyde-free flavorant;
d.) wherein the composition is free of sodium benzoate, sorbates, salts of edetate (EDTA), benzaldionium chloride and parabens and further comprises less than 2.5% wt/wt total isoquinolines and maintains said level of isoquinolines for at least 24 months; and
e.) wherein the tablet is formed in the absence of liquid water at substantially ambient temperature.

8. The chewable tablet of claim 7, wherein the composition further comprises less than 1.5% wt/wt total isoquinolines and maintains said level of isoquinolines for at least 24 months.

9. The composition of claim 7, wherein the matrix comprises at antioxidant.

10. The composition of claim 9, wherein the antioxidant is propyl gallate.

11. The composition of claim 7, wherein the matrix comprises mannitol.

12. A method of treating an mammal in need of treatment comprising providing an effective amount of a chewable according to claim 1.

13. A chewable tablet comprising:
a). about 2.5 mg/du of phenylephrine;
b). from about 1% wt/wt to about 10% wt/wt sucralose;
c.) about 1 mg/du brompheniramine maleate;
d). a matrix comprising substantially aldehyde-free excipients and an aldehyde-free flavorant; and
e.) wherein the composition is preservative free and further comprises less than 2.5 % wt/wt total isoquinolines and maintains said level of isoquinolines for at least 24 months.

* * * * *